(12) United States Patent
Burd Mehta

(10) Patent No.: US 7,521,186 B2
(45) Date of Patent: Apr. 21, 2009

(54) PCR COMPATIBLE NUCLEIC ACID SIEVING MATRIX

(75) Inventor: Tammy Burd Mehta, San Jose, CA (US)

(73) Assignee: Caliper Lifesciences Inc., Mountain View, CA (US)

( * ) Notice: Subject to any disclaimer, the term of this patent is extended or adjusted under 35 U.S.C. 154(b) by 252 days.

(21) Appl. No.: 10/659,423

(22) Filed: Sep. 10, 2003

(65) Prior Publication Data

US 2004/0045827 A1    Mar. 11, 2004

Related U.S. Application Data

(62) Division of application No. 09/792,297, filed on Feb. 23, 2001, now abandoned.

(60) Provisional application No. 60/190,773, filed on Mar. 20, 2000.

(51) Int. Cl.
*C12Q 1/68* (2006.01)
*C12P 19/34* (2006.01)

(52) U.S. Cl. .......................................... 435/6; 435/91.2

(58) Field of Classification Search .................... 435/6, 435/91.2
See application file for complete search history.

(56) References Cited

U.S. PATENT DOCUMENTS

| | | | |
|---|---|---|---|
| 4,390,403 A | 6/1983 | Batchelder | |
| 4,683,202 A | 7/1987 | Mullis | |
| 4,908,112 A | 3/1990 | Pace | |
| 5,126,022 A | 6/1992 | Soane et al. | |
| 5,135,855 A * | 8/1992 | Moss et al. | 435/69.1 |
| 5,164,055 A * | 11/1992 | Dubrow | 204/455 |
| 5,188,963 A * | 2/1993 | Stapleton | 435/288.3 |
| 5,264,101 A | 11/1993 | Demorest et al. | |
| 5,426,039 A | 6/1995 | Wallace et al. | |
| 5,498,392 A | 3/1996 | Wilding et al. | |
| 5,571,410 A | 11/1996 | Swedberg | |
| 5,585,069 A | 12/1996 | Zanzucchi et al. | |
| 5,587,128 A | 12/1996 | Wilding et al. | |
| 5,593,838 A | 1/1997 | Zanzucchi et al. | |
| 5,603,351 A | 2/1997 | Cherukuri et al. | |
| 5,616,478 A * | 4/1997 | Chetverin et al. | 435/91.2 |
| 5,635,358 A | 6/1997 | Wilding et al. | |
| 5,637,469 A | 6/1997 | Wilding et al. | |
| 5,699,157 A | 12/1997 | Parce | |
| 5,716,825 A | 2/1998 | Hancock et al. | |
| 5,750,015 A | 5/1998 | Soane et al. | |
| 5,770,029 A | 6/1998 | Nelson et al. | |
| 5,779,868 A | 7/1998 | Parce et al. | |
| 5,800,690 A | 9/1998 | Chow et al. | |
| 5,842,787 A | 12/1998 | Kopf-Sill et al. | |
| 5,852,495 A | 12/1998 | Parce | |
| 5,856,174 A * | 1/1999 | Lipshutz et al. | 435/286.5 |
| 5,869,004 A | 2/1999 | Parce et al. | |
| 5,874,212 A | 2/1999 | Prockop et al. | |
| 5,876,675 A | 3/1999 | Kennedy | |
| 5,880,071 A | 3/1999 | Parce et al. | |
| 5,882,465 A | 3/1999 | McReynolds | |
| 5,885,470 A | 3/1999 | Parce et al. | |
| 5,942,443 A | 8/1999 | Parce et al. | |
| 5,948,227 A | 9/1999 | Dubrow | |
| 5,955,028 A | 9/1999 | Chow | |
| 5,957,579 A | 9/1999 | Kopf-Sill et al. | |
| 5,958,203 A | 9/1999 | Parce et al. | |
| 5,958,694 A | 9/1999 | Nikiforov | |
| 5,959,291 A | 9/1999 | Jensen | |
| 5,964,995 A | 10/1999 | Nikiforov et al. | |
| 5,965,001 A | 10/1999 | Chow et al. | |
| 5,965,410 A | 10/1999 | Chow et al. | |
| 5,972,187 A | 10/1999 | Parce et al. | |
| 5,976,336 A | 11/1999 | Dubrow et al. | |
| 5,989,402 A | 11/1999 | Chow et al. | |
| 6,001,231 A | 12/1999 | Kopf-Sill | |
| 6,004,515 A | 12/1999 | Parce et al. | |
| 6,007,690 A | 12/1999 | Nelson et al. | |
| 6,011,252 A | 1/2000 | Jensen | |
| 6,012,902 A | 1/2000 | Parce | |
| 6,013,166 A | 1/2000 | Heller | |
| 6,042,710 A | 3/2000 | Dubrow | |
| 6,046,056 A | 4/2000 | Parce et al. | |

(Continued)

FOREIGN PATENT DOCUMENTS

WO    WO-96/04547    2/1996

(Continued)

OTHER PUBLICATIONS

Waters et al. Microchip Device for Cell Lysis, Multiplex PCR Amplification, and Electrophoretic Sizing. Anal Chem. Jan. 1, 1998; 70(1): pp. 158-162.*

(Continued)

*Primary Examiner*—Kenneth R. Horlick
*Assistant Examiner*—Christopher M. Babic
(74) *Attorney, Agent, or Firm*—Cardinal Law Group

(57) ABSTRACT

Sieving mediums comprising less than about 0.5% polymer, less than about 0.4% polymer, and 0.35% polymer or less are used to perform nucleic acid separations and PCR. The low polymer concentration does not inhibit PCR reactions and is sufficient for performing nucleic acids separations. Microfluidic devices are used to perform nucleic acids separations and PCR reactions in the sieving mediums described.

9 Claims, 3 Drawing Sheets

U.S. PATENT DOCUMENTS

| | | | |
|---|---|---|---|
| 6,068,752 | A | 5/2000 | Dubrow et al. |
| 6,071,478 | A | 6/2000 | Chow |
| 6,074,725 | A | 6/2000 | Kennedy |
| 6,080,295 | A | 6/2000 | Parce et al. |
| 6,306,590 | B1 * | 10/2001 | Mehta et al. ............... 435/6 |
| 6,395,887 | B1 * | 5/2002 | Weissman et al. .......... 536/23.1 |
| 6,455,682 | B1 | 9/2002 | Barron |
| 6,706,162 | B1 * | 3/2004 | Voss et al. ................. 204/455 |

FOREIGN PATENT DOCUMENTS

| | | |
|---|---|---|
| WO | WO-97/02357 | 1/1997 |
| WO | WO-98/00231 | 1/1998 |
| WO | WO 98/00231 A | 1/1998 |
| WO | WO-98/00705 | 1/1998 |
| WO | WO-98/00707 | 1/1998 |
| WO | WO-98/02728 | 1/1998 |
| WO | WO 98/04909 A | 2/1998 |
| WO | WO-98/05424 | 2/1998 |
| WO | WO-98/22811 | 5/1998 |
| WO | WO-98/45481 | 10/1998 |
| WO | WO-98/45929 | 10/1998 |
| WO | WO-98/46438 | 10/1998 |
| WO | WO-98/49548 | 11/1998 |
| WO | WO-98/55852 | 12/1998 |
| WO | WO-98/56505 | 12/1998 |
| WO | WO-98/56956 | 12/1998 |
| WO | WO-99/00649 | 1/1999 |
| WO | WO-99/10735 | 3/1999 |
| WO | WO-99/12016 | 3/1999 |
| WO | WO-99/16162 | 4/1999 |
| WO | WO-99/19056 | 4/1999 |
| WO | WO-99/19516 | 4/1999 |
| WO | WO-99/29497 | 6/1999 |
| WO | WO-99/31495 | 6/1999 |
| WO | WO-99/34205 | 6/1999 |
| WO | WO-99/43432 | 9/1999 |
| WO | WO-99/44217 | 9/1999 |
| WO | WO-99/56954 | 11/1999 |
| WO | WO-99/64848 | 12/1999 |
| WO | WO-00/09753 | 2/2000 |
| WO | WO-00/50172 | 8/2000 |
| WO | WO-00/60108 | 10/2000 |
| WO | WO-01/14064 | 3/2001 |

OTHER PUBLICATIONS

Moreira ("Efficient removal of PCR inhibitors using agarose-embedded DNA preparations" Nucleic Acids Research. 1998. vol. 26, No. 13: pp. 3309-3310).*

Woolley et al. "Ultra-high-speed DNA fragment separations using microfabricated capillary array electrophoresis chips" Proc. Natl. Acad. Sci. Nov. 1994. vol. 91: pp. 11348-11352).*

Maniatis et al. Molecular cloning: a laboratory Manual. Cold Spring Harbor Laboratory Press, Cold Spring Harbor, NY (1982): pp. 150-152.*

Moreira ("Efficient removal of PCR inhibitors using agarose-embedded DNA preparations" Nucleic Acids Research. 1998. vol. 26, No. 13: pp. 3309-3310).*

Maniatis et al. Molecular cloning: a laboratory Manual. Cold Spring Harbor Laboratory Press, Cold Spring Harbor, NY (1982): pp. 150-152.*

Woolley et al. "Ultra-high-speed DNA fragment separations using microfabricated capillary array electrophoresis chips" Proc. Natl. Acad. Sci. Nov. 1994. vol. 91: pp. 11348-11352).*

Mitra et al. ("In situ localized amplification and contact replication of many individual DNA molecules" Nucleic Acids Res. Dec. 15, 1999;27(24):e34).*

Woolley et al. ("Functional integration of PCR amplification and capillary electrophoresis in a microfabricated DNA analysis device" Anal Chem. Dec. 1, 1996;68(23):4081-6).*

Barringer et al. "Blunt-end and single-strand ligations by *Escherichia coli* Ligase: influence on an in vitro amplification scheme," *Gene* (1990) 89(1):117-122.

Beskin et al. "On the mechanism of the modular primer effect" *Nucl. Acids Res.* (1995) 23(15):2881-2885.

Cheng et al. *Nature* (1994) 369:684-685.

Cohen, C.B. et al. "A Microchip-Based Enzyme Assay for Protein Kinase A" *Anal. Chem.* (1999) 273:89-97.

Dasgupta, P.G. et al., "Electroosmosis: A Reliable Fluid Propulsion System for Flow Injection Analysis" *Anal. Chem.* (1994) 66:1792-1798.

Effenhauser et al. "High-speed separation of antisense oligonucleotides on a micromachined capillary electrophoresis device" *Anal. Chem.* (1994) 66:2949-2953.

Fouassier et al. Polymerisation induite sous irradiation laser visible *Makromol. Chem.* (1991) 192:245-260.

Guatelli et al., *PNAS* (1990) 87:1874.

Hagiwara et al. "Long distance sequencer method: a novel strategy for large DNA sequencing projects" *Nucl. Acids Res.* (1996) 24(12):2460-2461.

Ike et al., "Electrostatic and Hydrodynamic Separation of DNA Fragments in Capillary Tubes" *Anal. Chem.* (1996) 68:4321-4325.

Jacobson, S.C. et al., "Fused Quartz Substrates for Microchip Electrophoresis" *Anal. Chem.* (1995) 67:2059-2063.

Kwoh et al., *PNAS* (1990) 86:1173.

Landegren et al. *Science* (1988) 241:1077-1080.

Lantz et al., "Detection of Pathogenic *Yersinia enterocolitica* in Enrichment Media and Pork by a Multiplex PCR: A Study of Sample Preparation and PCR-inhibitory Components" *Int'l. J. Food Microbiol.* (1998) 45:93-105.

Manz, A. et al., "Electroosmotic pumping and electrophoretic separations for miniaturized chemical analysis systems," *J. Micromech. Microeng.* (1994) 4:257-265.

Neckers et al. "Photopolymerization using derivatives of fluorescent" *Polym. Material Sci. Eng.* (1989) 60:15.

Porter et al. "Direct PCR sequencing with boronated nucleotides" *Nucl. Acids Res.* (1997) 25(8):1611-1617.

Raja et al. "DNA sequencing using differential extension with nucleotide subsets (DENS)" *Nucl. Acids Res.* (1997) 25(4):800-805.

Ramsey, J.M. et al., "Microfabricated chemical measurement systems" *Nature Med.* (1995) 1:1093-1096.

Seiler, K. et al., "Planar Glass Chips for Capillary Electrophoresis: Repetitive Sample Injection, Quantitation, and Separation Efficiency" *Anal. Chem.* (1993) 65:1481-1488.

Seiler, K. et al., "Electroosmotic Pumping and Valveless Control of Fluid Flow Within a Manifold of Capillaries on a Glass Chip" *Anal. Chem.* (1994) 66:3485-3491.

Sooknanan et al., *Biotechnology* (1995) 13:563-564.

Sundberg, S.A. "High-Throughput and Ultra-High-Throughput Screening: solution—and cell-based approaches" *Curr. Opin. Biotech.* (2000) 11:47-53.

Van Brunt *Biotechnology* (1990) 8:291-294.

Watson et al., "Purification and Characterization of a Common Soil Component which Inhibits the Polymerase Chain Reaction," *Can. J. Microbiol.*(2000) 46:632-642.

Wilding et al. "PCR in a silicon microstructure" *Clin. Chem.* (1994) 40(9):1815-1818.

Witt et al., "Techniques for the Evaluation of Nucleic Acid Amplification technology Performance with Specimens Containing Interfering Substances: Efficacy of boom Methodology for Extraction of HIV-1 RNA" *J. Virological Methods* (1999) 79:97-111.

Woolley et al. "Ultra-high-speed DNA fragment separations using microfabricated capillary array electrophoresis chips" *PNAS USA* (1994) 91:11348-11352.

Wu et al., *Genomics* (1989) 4:560-569.

* cited by examiner

US 7,521,186 B2

PCR COMPATIBLE NUCLEIC ACID SIEVING MATRIX

CROSS-REFERENCE TO RELATED APPLICATIONS

This application is a divisional of U.S. patent application Ser. No. 09/792,297, filed Feb. 23, 2001, which claims benefit of and priority to U.S. Ser. No. 60/190,773, entitled "PCR COMPATIBLE NUCLEIC ACID SIEVING MEDIUM," filed Mar. 20, 2000 by Burd Mehta.

BACKGROUND OF THE INVENTION

Manipulating fluidic reagents and assessing the results of reagent interactions are central to chemical and biological science. Manipulations include mixing fluidic reagents, assaying products resulting from such mixtures, separation or purification of products and reagents, and the like. A single experiment may involve hundreds of fluidic manipulations, product separations, recording processes and the like, each of which involve different types of laboratory equipment and conditions.

One particularly labor intensive biochemical series of laboratory fluidic manipulations is nucleic acid synthesis and analysis. A variety of in vitro amplifications methods for biochemical synthesis of nucleic acids are available, such as the polymerase chain reaction (PCR). See, Mullis et al., (1987) U.S. Pat. No. 4,683,202 and PCR protocols: A Guide to Methods and Applications (Innis et al. eds., Academic Press Inc. San Diego Calif. (1990). PCR methods typically require the use of specialized machinery for performing thermocycling reactions for DNA synthesis followed by the use of special machinery for the electrophoretic analysis of synthesized nucleic acids.

Various strategies have been used to increase laboratory throughput. For example, microscale devices for high throughput mixing and assaying small fluid volumes have been developed. See, e.g., Parce et al., U.S. Pat. No. 5,942,443, which provides pioneering technology related to microscale devices. In particular, U.S. Pat. No. 6,306,590 provides methods of performing PCR and nucleic acid separations in the same microfluidic device.

Improved methods for performing PCR and nucleic acid separations including improved sieving mediums are desirable, particularly those which take advantage of high-throughput, low cost microfluidic systems. The present invention provides these and other features by providing nucleic acid sieving mediums, methods of performing PCR and nucleic acid separations along with high throughput microscale systems and many other features that will be apparent upon complete review of the following disclosure.

SUMMARY OF THE INVENTION

The present invention provides nucleic acid sieving mediums, microfluidic devices, and methods for performing nucleic acid separations and PCR. The sieving mediums provided are compatible with both nucleic acid separations and PCR because they provide baseline nucleic acid separation and do not inhibit PCR.

In one aspect, a microfluidic device for performing both PCR and nucleic acid separations is provided. The device comprises at least one microscale channel and a sieving medium. The sieving medium is disposed within the at least one microscale channel and comprises a polymer solution, which polymer solution comprises less than about 0.5% polymer, less than about 0.4% polymer, or about 0.35% polymer or less.

Typical polymers include acrylamide, such as linear acrylamide, polyacrylamide, polydimethylacrylamide, polydimethylacrylamide/coacrylic acid, and the like. Other polymers include, but are not limited to, agarose, methyl cellulose, polyethylene oxide, hydroxycellulose, hydroxy ethyl cellulose, and the like.

The devices also optionally comprise one or more proteins, nucleic acids, PCR reaction components, or PCR products disposed within the at least one microfluidic channel. PCR reaction components include, but are not limited to, a polymerase, e.g., a thermostable DNA polymerase, a plurality of nucleotides, a nucleic acid template, a primer which hybridizes to the nucleic acid template, and $Mg^{++}$.

In a second aspect, methods of separating polynucleotides are provided. In one embodiment, the method comprises providing two or more polynucleotides and a sieving medium. The polynucleotides typically comprise one or more PCR products, RNA, or DNA. The sieving medium typically comprises a polymer solution as described above. The two or more polynucleotides migrate through the sieving medium, thereby separating the two or more polynucleotides.

In another embodiment, the sieving medium is introduced into a microfluidic channel and the two or more polynucleotides migrate through the sieving medium in the microfluidic channel. For example, the two or more polynucleotides are optionally separated by electrophoresis in the sieving medium.

In a third aspect, methods of performing PCR and separating one or more PCR products are provided. The methods comprise mixing one or more PCR reaction component as described above with a sieving medium to provide a PCR sieving medium, wherein the sieving medium comprises a polymer solution as described above. The PCR sieving medium is then thermocycled to produce one or more PCR products, which are separated by flowing in the sieving medium.

In another embodiment, PCR is performed in a microfluidic device by mixing the PCR reaction components with the sieving medium in a microfluidic channel. The one or more PCR products are separated, e.g., electrophoretically, by flowing the one or more PCR products through the sieving medium in the microfluidic channel.

In a fourth aspect, nucleic acid sieving mediums are provided. The sieving mediums comprise one or more polynucleotides, such as DNA, RNA, PCR products, or the like, one or more PCR reagents as described above, and a polymer solution as described above.

DETAILED DISCUSSION OF THE INVENTION

Figure 1:
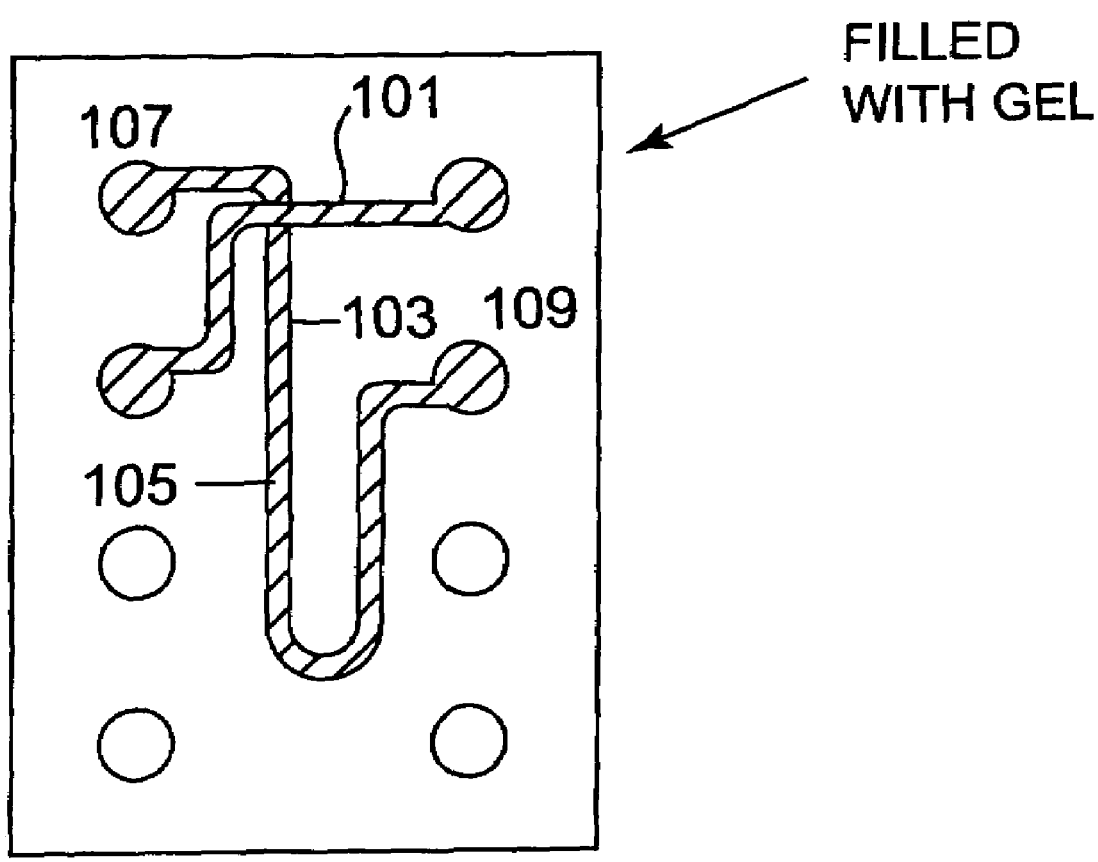
FIG. 1 is a schematic drawing of a microfluidic device for performing PCR and nucleic acid separations.

DNA separations are normally performed in sieving mediums that have a certain concentration of sieving medium to achieve separation of various sizes of DNA fragments. The concentration of polymers used in sieving media typically inhibits the polymerase chain reaction (PCR), thereby preventing the two assays from being carried out in one medium. The present invention provides a mixture compatible with PCR that also serves as a DNA separation medium. The sieving mediums of the present invention comprise lower concentrations of polymer than are normally used to achieve DNA separation. The lower concentrations of polymer do not inhibit PCR and still provide separation of polynucleotides.

A typical sieving polymer concentration used in DNA separations is about 3%, e.g., 3% acrylamide. This concentration is known to inhibit polymerase chain reactions (PCR). However, lower levels of the same polymer are not inhibitory. The present invention provides a PCR compatible mixture with a low amount of polymer used to suppress electroosmotic flow in the channels of a microfluidic device. The concentration of polymer provided in the present invention is typically less than about 0.5%, more typically less than about 0.4% and preferably about 0.35% or less. Since this is below the usual threshold of sieving, the polymer here was initially used as an agent to eliminate bulk movement of the fluid by acting as a dynamic coating for the channel walls.

However, the present sieving medium also provided nucleic acid separations in the same low polymer medium in which PCR was performed. While, the exact mechanism of DNA sieving is not known, one advantage of the present medium is to provide a single fluid compatible with PCR and nucleic acid separations. Thus, the present invention provides, with a relatively simple loading or fabrication procedure, multi-step assays, e.g., PCR and subsequent product separation, using the present sieving medium.

The present invention provides a nucleic acid sieving medium compatible with nucleic acid separations and PCR as well as devices for performing nucleic acid separations and PCR, e.g., devices comprising a sieving medium with a low polymer concentration. Methods of separating nucleic acids and performing PCR using low concentration sieving mediums are also provided.

I. PCR Compatible Sieving Mediums

A nucleic acid sieving medium that is compatible with PCR and nucleic acid separations is provided. The sieving medium comprises a low concentration of polymer, which low concentration does not inhibit PCR. Typically DNA is separated in sieving mediums with higher polymer concentrations than those provided herein. However, nucleic acids are optionally separated using the lower polymer concentrations provided herein thereby providing methods for performing nucleic acid separation and PCR in the same medium.

The sieving medium typically comprises one or more polynucleotides, one or more PCR reagents, and a polymer solution, which polymer solution comprises less than about 0.5% polymer, less than about 0.4% polymer, or about 0.35% polymer or less. The polymer solution is thereby used to provide PCR and nucleic acid separations in the same matrix. In some embodiments, the polymer solution is eliminated and optionally replaced with an electroosmotic flow suppressor.

The one or more PCR reaction components comprise one or more of: a thermostable polymerase, a thermostable DNA polymerase, a plurality of nucleotides, a nucleic acid template, a primer which hybridizes to the nucleic acid template, $Mg^{++}$, and the like. The one or more polynucleotides typically comprise DNA, RNA, or PCR products.

Typical polymer solutions of the invention comprise low concentrations of one or more of the following: acrylamide, agarose, methyl cellulose, polyethylene oxide, hydroxycellulose, hydroxy ethyl cellulose, or the like. Combinations of any of these polymers are also optionally used. Various types of acrylamide are used, including, but not limited to, linear acrylamide, polyacrylamide, polydimethylacrylamide, polydimethylacrylamide/coacrylic acid, or the like.

A wide variety of alternative sieving mediums are available, and are optionally used in methods of the invention, e.g., at low concentrations to provide a medium compatible with both PCR and nucleic acid separations. For example, a variety of sieving matrixes and the like are available from Supelco, Inc. (Bellefonte, Pa.; see, 1997 Suppleco catalogue). Common matrixes which are useful in the present invention include those generally used in low pressure liquid chromatography, gel electrophoresis and other liquid phase separations; matrix materials designed primarily for non-liquid phase chromatography are also useful in certain contexts, as the materials often retain separatory characteristics when suspended in fluids. For a discussion of electrophoresis see, e.g., Weiss (1995) *Ion Chromatography* VCH Publishers Inc.; Baker (1995) *Capillary Electrophoresis* John Wiley and Sons; Kuhn (1993) *Capillary Electrophoresis: Principles and Practice* Springer Verlag; Righetti (1996) *Capillary Electrophoresis in Analytical Biotechnology* CRC Press; Hill (1992) *Detectors for Capillary Chromatography* John Wiley and Sons; *Gel Filtration: Principles and Methods (5th Edition)* Pharmacia; Gooding and Regnier (1990) *HPLC of Biological Macromolecules: Methods and Applications* (Chrom. Sci. Series, volume 51) Marcel Dekker and Scott (1995) *Techniques and Practices of Chromatography* Marcel Dekker, Inc.

Alternate separation matrix media include, but are not limited to, low pressure liquid chromatography media include, e.g., non-ionic macroreticular and macroporous resins which adsorb and release components based upon hydrophilic or hydrophobic interactions such as Amberchrom resins (highly cross-linked styrene/divinylbenzene copolymers suitable for separation of peptides, proteins, nucleic acids, antibiotics, phytopharmacologicals, and vitamins); the related Amberlite XAD series resins (polyaromatics and acrylic esters) and amberchroms (polyaromatic and polymethacrylates) (manufactured by Rohm and Haas, available through Suppleco); Diaion (polyaromatic or polymethacrylic beads); Dowex (polyaromatics or substituted hydrophilic functionalized polyaromatics) (manufactured by Dow Chemical, available through Suppleco); Duolite (phenol-formaldehyde with methanolic functionality), MCI GEL sephabeads, supelite DAX-8 (acrylic ester) and Supplepak (polyaromatic) (all of the preceding materials are available from Suppleco). For a description of uses for Amberlite and Duolite resins, see, *Amberlite/Duolite Anion Exchange Resins* (Avaliable from Suppleco, Cat No. T412141). Gel filtration chromatography matrixes are also suitable, including sephacryl, sephadex, sepharose, superdex, superose, toyopearl, agarose, cellulose, dextrans, mixed bead resins, polystyrene, nuclear resins, DEAE cellulose, Benzyl DEA cellulose, TEAE cellulose, and the like (Suppleco).

Other electrophoresis media include silica gels such as Davisil Silica, E. Merck Silica Gel, Sigma-Aldrich Silica Gel (all available from Suppleco) in addition to a wide range of silica gels available for various purposes as described in the Aldrich catalogue/handbook (Aldrich Chemical Company (Milwaukee, Wis.)). Preferred gel materials include agarose based gels, various forms of acrylamide based gels, Genescan polymers (reagents available from, e.g., Suppleco, SIGMA, Aldrich, SIGMA-Aldrich and many other sources), colloidial solutions such as protein colloids (gelatins) and hydrated starches. Various forms of gels are discussed further below.

A variety of affinity media for purification and separation of molecular components are also available, including a variety of modified silica gels available from SIGMA, Aldrich and SIGMA-Aldrich, as well as Suppleco, such as acrylic beads, agarose beads, cellulose, sepharose, sepharose CL, toyopearl, or the like chemically linked to an affinity ligand such as a biological molecule. A wide variety of activated matrixes, amino acid resins, avidin and biotin resins, carbohydrate resins, dye resins, glutathione resins, hydrophobic resins, immunochemical resins, lectin resins, nucleotide/coenzyme resins, nucleic acid resins, and specialty resins are available, e.g., from Suppleco, SIGMA, Aldrich or the like. See also, Hermanson et al. (1992)*Immobilized Affinity Ligand Techniques* Academic Press and optionally used in the channels of the invention.

Other media commonly used in chromatography are also adaptable to the present invention, including activated aluminas, carbopacks, carbosieves, carbowaxes, chromosils, DEGS, Dexsil, Durapak, Molecular Sieve, OV phases, pourous silica, chromosorb series packs, HayeSep series, Porapak series, SE-30, Silica Gel, SP-1000, SP-1200, SP-2100, SP-2250, SP-2300, SP-2401, Tenax, TCEP, supelcosil LC-18-S and LC-18-T, Methacrylate/DVBm, polyvinylalcohols, napthylureas, non-polar methyl silicone, methylpolysiloxane, poly (ethylene glycol) biscyanopropyl polysiloxane and the like.

Other types of separation matrices are also optionally used and discussed in U.S. Pat. No. 6,306,590. For a review of chromatography techniques and media, see, e.g., Affinity Chromatography—A Practical Approach, Dean et al., (Eds.) IRL Press, Oxford (1985); and, Chromatographic Methods, $5^{th}$ Edition, Braithwaite et al., (1996).

Many of the materials used to provide the sieving mediums of the invention are supplied in a liquid or fluidic phase and then polymerized to provide a sieving matrix. In one embodiment, the fluid polymerizes upon exposure to light (i.e., the fluid comprises a "photopolymerizable" polymer). The fluid is then selectively exposed to light (e.g., using photomasking techniques) in those regions where a polymerized gel is desired. Unpolymerized fluid is then optionally washed out of the unselected regions of the microfluidic device, or into a waste reservoir using electrokinetic flow or pressure.

A wide variety of free-radical polymerizable monomers photopolymerize to form gels, or can be made photopolymerizeable by the addition of, e.g., energy transfer dyes. For example, free-radical polymerizable monomers can be selected from acrylate, methacrylate and vinyl ester functionalized materials. They can be monomers and/or oligomers such as (meth)acrylates (meth)acrylamides, acrylamides, vinyl pyrrolidone and azalactones. Such monomers include mono-, di-, or poly-acrylates and methacrylates such as methyl acrylate, methyl methacrylate, ethyl acrylate, isopropyl methacrylate, isooctyl acrylate, isobornyl acrylate, isobornyl methacrylate, acrylic acid, n-hexyl acrylate, stearyl acrylate, allyl acrylate, glycerol diacrylate, glycerol triacrylate, ethylene glycol diacrylate, diethyleneglycol diacrylate, triethyleneglycol dimethacrylate, 1,6-hexanediol diacrylate, 1,3-propanediol diacrylate, 1,3-propanediol dimethacrylate, trimethanol triacrylate, 1,2,4-butanetriol trimethylacrylate, 1,4-cyclohexanediol diacrylate, pentaerythritol triacrylate, pentaerythritol tetraacrylate, pentaerythritol tetramethacrylate, sorbitol hexacrylate, bis[1-(2-acryloxy)]-p-ethoxyphenyl-dimethylmethane, bis[1-(3-acryloxy-2-hydroxy)]-propoxyphenyl dimethylmethane, tris-hydroxyethyl isocyanurate trimethacrylate; the bisacrylates and bis-methacrylates of polyethylene glycols of molecular weight 200-500, copolymerizable mixtures of acrylated monomers, acrylated oligomers, PEG diacrylates, etc. Strongly polar monomers such as acrylic acid, acrylamide, itaconic acid, hydroxyalkyl acrylates, or substituted acrylamides or moderately polar monomers such as N-vinyl-2-pyrrolidone, N-vinyl caprolactam, and acrylonitrile are also useful.

Proteins such as gelatin, collagen, elastin, zein, and albumin, whether produced from natural or recombinant sources, which are made by free-radical polymerization by the addition of carbon-carbon double or triple bond-containing moieties, including acrylate, diacrylate, methacrylate, ethacrylate, 2-phenyl acrylate, 2-chloro acrylate, 2-bromo acrylate, itaconate, oliogoacrylate, dimethacrylate, oligomethacrylate, acrylamide, methacrylamide, styrene groups, and other biologically acceptable photopolymerizable groups, can also be used, e.g., in low concentration, to form sieving matrixes.

Dye-sensitized polymerization is well known in the chemical literature. For example, light from an argon ion laser (514 nm), in the presence of an xanthin dye and an electron donor, such as triethanolamine, to catalyze initiation, serves to induce a free radical polymerization of acrylic groups in a reaction mixture (Neckers, et al., (1989) *Polym. Materials Sci. Eng.,* 60: 15; Fouassier, et al., (1991) *Makromol. Chem.,* 192:245-260). After absorbing laser light, the dye is excited to a triplet state. The triplet state reacts with a tertiary amine such as the triethanolamine, producing a free radical which initiates a polymerization reaction. Polymerization is extremely rapid and is dependent on the functionality of the composition, its concentration, light intensity, and the concentration of dye and, e.g., amine.

Dyes are also optionally used which absorb light having a frequency between 320 nm and 900 nm, form free radicals, are water soluble, etc. There are a large number of photosensitive dyes that are optionally used to optically initiate polymerization, such as ethyl eosin, eosin Y, fluorescein, 2,2-dimethoxy-2-phenyl acetophenone, 2-methoxy,2-phenylacetophenone, camphorquinone, rose bengal, methylene blue, erythrosin, phloxime, thionine, riboflavin, methylene green, acridine orange, xanthine dye, and thioxanthine dyes.

Cocatalysts useful with photoinitiating dyes are typically nitrogen based compounds capable of stimulating a free radical reaction. Primary, secondary, tertiary or quaternary amines are suitable cocatalysts, as are nitrogen atoms containing electron-rich molecules. Cocatalysts include triethanolamine, triethylamine, ethanolamine, N-methyl diethanolamine, N,N-dimethyl benzylamine, dibenzyl amine, N-benzyl ethanolamine, N-isopropyl benzylamine, tetramethyl ethylenediamine, potassium persulfate, tetramethyl ethylenediamine, lysine, ornithine, histidine and arginine. Examples of the dye/photoinitiator system include ethyl eosin with an amine, eosin Y with an amine, 2,2-dimethoxy-2-phenoxyacetophenone, 2-methoxy-2-phenoxyacetophenone, camphorquinone with an amine, and rose bengal with an amine.

In some cases, dye may absorb light and initiate polymerization, without any additional initiator such as an amine. In these cases, only the dye and a monomer need be present to initiate polymerization upon exposure to light. The generation of free radicals is terminated when the laser light is removed. Some photoinitiators, such as 2,2-dimethoxy-2-phenylacetophenone, do not require any auxiliary amine to induce photopolymerization; in these cases, the presence of dye, monomer, and an appropriate wavelength of light is sufficient for photopolymerization.

Preferred light sources include various lamps and lasers such as those which have a wavelength of about 320-800 nm. This light can be provided by any appropriate source able to generate the desired radiation, such as a mercury lamp, long-wave UV lamp, He-Ne laser, an argon ion laser, etc. In a preferred embodiment, a UV source is used to polymerize a UV photopolymerizeable gel. Similarly, the light source used is typically selected based upon the chemistry which is to be affected by the source.

Similarly, a variety of gels or polymers are selectively polymerized by exposure to heat. As described herein, selective heat control using applied current is easily performed in the microfluidic apparatus of the invention, providing for simplified control of gel polymerization through thermal processes. Examples include initiation by thermal initiators, which form free radicals at moderate temperatures, such as benzoyl peroxide, with or without triethanolamine, potassium persulfate, with or without tetramethylethylenediamine, and ammonium persulfate with sodium bisulfite.

In another embodiment, the fluid is polymerized by selectively exposing it to an activator or cross-linker. For example, where the fluid is polyacrylamide, the activator/cross linker can be TEMED and/or APS.

The above polymers, e.g., in solution format, gel format, or the like, and typically polymerized as described above, are typically used in microfluidic devices to provide devices useful for both PCR and separation of nucleic acids.

II. Separating Nucleic Acids in a Polymer Sieving Medium

A mixture of polynucleotides, e.g., DNA or RNA molecules or fragments thereof, PCR products, sequencing reaction products, and the like, are separated by size and/or charge in a sieving medium, e.g., a sieving medium as described above. For example, the separation is typically an electrophoretic separation. The separated products are detected, often as they pass a detector (nucleic acids are typically labeled with radioactive nucleotides or fluorophores; accordingly appropriate detectors include spectrophotometers, fluorescent detectors, microscopes (e.g., for fluorescent microscopy) and scintillation counting devices). If the separated components are the products of a sequencing reaction, e.g., a chain termination method of sequencing, detection of size separated products is used to compile sequence information for the region being sequenced.

Typically electrophoretic separation is used to separate the mixture of components in the sample. Electrophoretic separation is the separation of substances achieved by applying an electric field to samples in a solution or gel, e.g., a polymer solution. In its simplest form, it depends on the different velocities with which the substances or components move in the field. The velocities depend, e.g., on the charge and size of the substances.

In a preferred embodiment, the polynucleotides are separated in a microscale separation channel or capillary. The separation channels or regions typically comprise a separation matrix, e.g., a polymerized sieving medium as discussed above. When the sample is flowed through the separation matrix, the components are separated, e.g., based on physical or chemical properties, such as molecular weight or charge. In the present invention, the sieving medium optionally comprises a gel or solution. In the present invention, the concentration of the polymer in the separation gel or solution is less than about 0.5%. Typically the concentration of the sieving medium is less than about 0.4% and more typically about 0.35% or less. In other embodiments, the polymer concentration can be greater than 0.5%, e.g., 0.55%, 0.6% or higher. See e.g., U.S. Pat. No. 6,306,590.

Preferably, the channel, such as channel 103 in FIG. 1, is a polyacrylamide gel filled channel or a polydimethylacrylamide/co-acrylic acid polymer filled channel on which the mixture of components is electrophoretically separated based on charge/mass ratio or molecular weight. Polyacrylamide used as a separation matrix in a microfluidic channel is optionally cross-linked or non-cross-linked. Preferably it is linear polyacrylamide, i.e., polydimethylacrylamide, polydimethylacrylamide/co-acrylic acid, or the like. Other polymers include cellulose, agarose, Genescan polymers, and the like.

For a review of electrophoretic separation techniques and polyacrylamide gels, see, e.g., The Encyclopedia of Molecular Biology, Kendrew (ed.) (1994); and, Gel Electrophoresis of Proteins: A Practical Approach, $2^{nd}$ edition Hames and Rickwood (Eds.) IRL Press, Oxford England, (1990).

A detector is optionally positioned so that it detects the polynucleotides, e.g., polynucleotides that are stained in the gel with a fluorescent nucleic acid stain. If the components are detected as they exit the separation region, the components are optionally identified by their retention times. The retention time of the oligonucleotides as they are electrophoresed through the sieving medium is used, e.g., in combination with markers to measure the molecular weight of and identify the polynucleotides.

Figure 3:
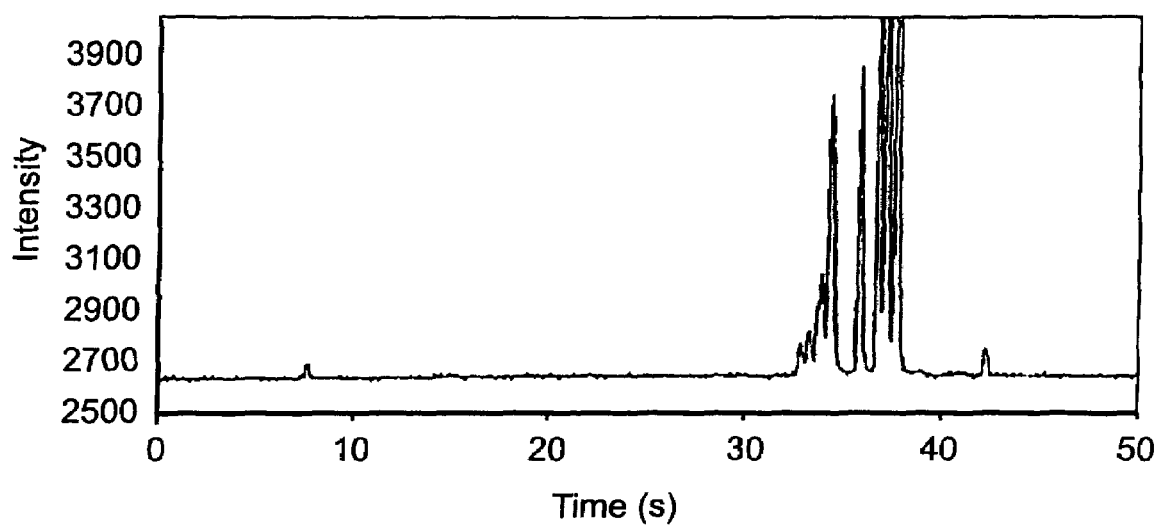
FIG. 3 is a graph providing nucleic acid separation data obtained in a sieving medium comprising 0.35% polymer.

FIG. 3 demonstrates baseline separation of polynucleotides achieved using the low polymer concentration sieving mediums of the present invention, e.g., a sieving medium comprising 0.35% polymer.

III. Performing PCR in a Sieving Medium

One aspect of the present invention is the surprising discovery that PCR can be performed in the same sieving matrix used to separate nucleic acids. For example, PCR is optionally performed in the presence of a low polymer sieving matrix, and the products of the PCR reaction are separable in the same sieving matrix, e.g., in a microfluidic channel.

Accordingly, in one aspect, the invention provides new methods of performing PCR. In the methods, components of a PCR reaction mixture (i.e., the molecules which participate in a PCR reaction, such as PCR extension primers, nucleotide triphosphates, thermostable enzymes, ions and buffer components such as $Mg^{++}$, template DNAs, etc.) are mixed with a sieving medium comprising less than about 0.5% polymer to provide a PCR sieving medium. Typically, the sieving medium comprises less than about 0.4% polymer. In a preferred embodiment, the sieving medium comprises about 0.35% polymer or less. In other embodiments, the sieving medium can comprise more than 0.5% polymer. The resulting mixture, e.g., the PCR sieving medium, is then repetitively thermocycled as described below to produce one or more PCR products, which are separated, e.g., electrophoretically, in the same sieving medium. Sieving mediums of use in performing PCR, e.g., with nucleic acid separation of the products, are described above.

Bench scale in vitro amplification techniques suitable for amplifying sequences to provide a nucleic acid e.g., as a diagnostic indicator for the presence of the sequence, or for subsequent analysis, sequencing or subcloning are known.

In brief, the most common form of in vitro amplification, i.e., PCR amplification, generally involves the use of one strand of the target nucleic acid sequence, e.g., the sequence to be amplified, as a template for producing a large number of complements to that sequence. Generally, two primer sequences complementary to different ends of a segment of the complementary strands of the target sequence hybridize with their respective strands of the target sequence, and in the presence of polymerase enzymes and nucleoside triphosphates, the primers are extended along the target sequence through the action of the polymerase enzyme (in asymmetric PCR protocols, a single primer is used). The extensions are melted from the target sequence by raising the temperature of the reaction mixture, and the process is repeated, this time with the additional copies of the target sequence synthesized in the preceding steps. PCR amplification typically involves repeated cycles of denaturation, hybridization and extension reactions to produce sufficient amounts of the target nucleic acid, all of which are carried out at different temperatures. Typically, melting of the strands, or heat denaturation, involves temperatures ranging from about 90° C. to 100° C. for times ranging from seconds to minutes. The temperature is then cycled down, e.g., to between about 40° C. and 65° C. for annealing of primers, and then cycled up to between about 70° C. and 85° C. for extension of the primers along the target strand. This process if referred to herein as "thermocycling."

Examples of techniques sufficient to direct persons of skill through in vitro amplification methods at benchtop scales, including the polymerase chain reaction (PCR) the ligase chain reaction (LCR), Qβ-replicase amplification and other RNA polymerase mediated techniques (e.g., NASBA) are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36-47; *The Journal Of NIH Research* (1991) 3, 81-94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077-1080; Van Brunt (1990) *Biotechnology* 8, 291-294; Wu and Wallace, (1989) *Gene* 4, 560; Barringer et al. (1990) *Gene* 89, 117, and Sooknanan and Malek (1995) *Biotechnology* 13: 563-564. Improved methods of cloning in vitro amplified nucleic acids are described in Wallace et al., U.S. Pat. No. 5,426,039. Improved methods of amplifying large nucleic acids by PCR are summarized in Cheng et al. (1994) *Nature* 369: 684-685 and the references therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, Ausbel, Sambrook and Berger, all supra.

In the present invention, the PCR reactants are mixed with a sieving medium comprising a low polymer concentration, e.g., 0.5% or less. The products are then directly separated, e.g., in a capillary, using the same sieving medium.

In preferred embodiments, the components of the PCR reaction mixture, e.g., a polymerase, nucleotides, and the like, are mixed with a sieving medium, e.g., with a low polymer concentration, in a microfluidic channel, e.g., a channel on a LABCHIP™, as described in more detail below. The apparatus optionally includes one or more additional channels crossing the microfluidic channel and optionally includes fluid (or joule heating) means such as an electrokinetic controller for thermocycling and fluid direction systems, e.g., electrokinetic controllers and/or pressure sources such as vacuum sources, for flowing materials and reagents through the channels. The PCR products are typically electrophoresed through the channels in the same sieving medium used to achieve product separation. Detection regions in the channels and corresponding detectors are also used, e.g., to detect the separated products.

IV. Microfluidic Devices Comprising a PCR Compatible Nucleic Acid Sieving Medium The sieving medium of the invention is typically used in a microfluidic device and the separation and PCR methods described above are preferably performed in a microfluidic device. The sieving medium is typically polymerized in a microscale channel of a microfluidic device, e.g., after the PCR reaction. Alternatively, dynamic sieving mediums, such as Genescan polymers, are used that do not require polymerization in the channel. PCR and separation of the products are both optionally performed in a sieving medium of the present invention in the channels of a microfluidic device.

A variety of microfluidic devices are optionally adapted for use in the present invention, e.g., by designing and configuring the channels as discussed below. These devices are described in various PCT applications and issued U.S. Patents by the inventors and their coworkers, including U.S. Pat. No. 5,699,157 (J. Wallace Parce) issued Dec. 16, 1997, U.S. Pat. No. 5,779,868 (J. Wallace Parce et al.) issued Jul. 14, 1998, U.S. Pat. No. 5,800,690 (Calvin Y. H. Chow et al.) issued Sep. 1, 1998, U.S. Pat. No. 5,842,787 (Anne R. Kopf-Sill et al.) issued Dec. 1, 1998, U.S. Pat. No. 5,852,495 (J. Wallace Parce) issued Dec. 22, 1998, U.S. Pat. No. 5,869,004 (J. Wallace Parce et al.) issued Feb. 9, 1999, U.S. Pat. No. 5,876,675 (Colin B. Kennedy) issued Mar. 2, 1999, U.S. Pat. No. 5,880,071 (J. Wallace Parce et al.) issued Mar. 9, 1999, U.S. Pat. No. 5,882,465 (Richard J. McReynolds) issued Mar. 16, 1999, U.S. Pat. No. 5,885,470 (J. Wallace Parce et al.) issued Mar. 23, 1999, U.S. Pat. No. 5,942,443 (J. Wallace Parce et al.) issued Aug. 24, 1999, U.S. Pat. No. 5,948,227 (Robert S. Dubrow) issued Sep. 7, 1999, U.S. Pat. No. 5,955,028 (Calvin Y. H. Chow) issued Sep. 21, 1999, U.S. Pat. No. 5,957,579 (Anne R. Kopf-Sill et al.) issued Sep. 28, 1999, U.S. Pat. No. 5,958,203 (J. Wallace Parce et al.) issued Sep. 28, 1999, U.S. Pat. No. 5,958,694 (Theo T. Nikiforov) issued Sep. 28, 1999, and U.S. Pat. No. 5,959,291 (Morten J. Jensen) issued Sept. 28, 199; and published PCT applications, such as, WO 98/00231, WO 98/00705, WO 98/00707, WO 98/02728, WO 98/05424, WO 98/22811, WO 98/45481, WO 98/45929, WO 98/46438, and WO 98/49548, WO 98/55852, WO 98/56505, WO 98/56956, WO 99/00649, WO 99/10735, WO 99/12016, WO 99/16162, WO 99/19056, WO 99/19516, WO 99/29497, WO 99/31495, WO 99/34205, WO 99/43432, and WO 99/44217.

In particular, the use of sieving mediums in PCR and nucleic acid separations in microfluidic devices is described in U.S. Pat. No. 6,306,590. In addition, various other elements are optionally included in the device, such as particle sets, separation gels, antibodies, enzymes, substrates, and the like. These optional elements are used in performing various assays, such as nucleic acid sequencing. For example, the use of particle sets in nucleic acid sequencing is described, e.g., in WO 00/50172, published Aug. 31, 2000, entitled "Manipulation of Microparticles In Microfluidic Systems," by Burd Mehta et al.

Complete integrated systems with fluid handling, signal detection, sample storage and sample accessing are also available. For example WO 98/00231 (supra) provides pioneering technology for the integration of microfluidics and sample selection and manipulation.

One aspect of the invention is the placement of the sieving medium in selected channels or channel regions of a microfluidic substrate. These materials (or precursors of the materials, e.g., monomers polymerized in the device as discussed above) are loaded into microfluidic components by electrokinesis, by pressurized pumping, by centrifugal force, or capillary flow. The present invention provides methods of DNA separation and PCR that are both compatible with the sieving mediums of the invention. Therefore, the sieving medium is typically loaded throughout the entire device. However if other assays are steps are desired, e.g., DNA sequencing reactions, certain channels are optionally filled with reagents for the desired assay or left empty Several methods of providing fluidic regions in selected regions of a channel, or selected channels are provided. In a first aspect, multiple microfluidic regions are filled with a sieving medium, e.g., in an unpolymerized solution that, upon polymerization, forms a sieving matrix. Elements of the microfluidic device such as microfluidic channels are filled with the sieving medium by forcing the fluid into the channel under pressure, or by moving the fluid into the channel electrokinetically. In one embodiment, the first fluid polymerizes upon exposure to light (i.e., the fluid comprises a "photopolymerizable" polymer). The fluid is then selectively exposed to light (e.g., using photomasking techniques) in those regions where a polymerized gel is desired. Unpolymerized fluid is then optionally washed out of the unselected regions of the microfluidic device, or into a waste reservoir using electrokinetic flow or pressure.

For either the thermal or photopolymerization methods herein, monomer is pumped, e.g., in aqueous buffer, into a channel or channel region using electroosmotic flow, or using a pressure gradient. After selective exposure to light or heat, as appropriate, unpolymerized materials are removed, typically using electroosmotic flow, but optionally using a pressure gradient, from regions where monomer material is undesirable.

In another embodiment, a sieving matrix is deposited throughout a channel or channels of a microfluidic device in a form which is subject to electroosmosis (i.e., the matrix moves electrokinetically in the channel).

In an additional embodiment, a sieving medium is loaded into multiple channels of a microfluidic device, e.g., under pressure, and polymerized in place. Selective components which solubilize the polymerized gel are then loaded (e.g., electrokinetically or under pressure) into channel regions where polymerized product is not desired, i.e., channels in which other assays are to be performed. The selected components dissolve the polymerized gel. Example of solubilization compounds include acids, bases and other chemicals. In one preferred embodiment, at least two compounds are used to dissolve polymerized products, where both products need to be present to dissolve the polymer. This provides for fine control of dissolution, e.g., where each chemical is under separate electrokinetic control. An example of such a chemical pair is DTT(N,N'-bis(acrylol)cystamine or (1,2-dihydroxyethylene-bis-acrylamide) [DHEBA] and sodium periodiate or calcium alginate+EDTA or TCEP-HCL and N,N'-bis (acryloyl)cystamine. A variety of such materials are known.

The sieving medium of the invention is particularly useful for performing experimental or diagnostic procedures which combine nucleic acid amplification and product separatory aspects. For example, PCR is performed in a microfluidic channel comprising a sieving medium as described herein, followed by separation in the same sieving medium, e.g., in the same or in a different channel region.

In one aspect, PCR or other thermal reaction reagents (e.g., LCR reagents) such as thermostable polymerase, DNA template, primers, nucleotides and buffers are mixed, e.g., with a sieving medium, in a microchannel or chamber, with the entire microfluidic substrate (e.g., a LABCHIP™ from Caliper Technologies) being subject to repeated cycles of heating and cooling, e.g., on a thermocycler or by switching between a hot plate and a heat sink.

In a second more preferred embodiment, variations in channel thickness and/or voltage are used selectively to heat selected regions of a channel which contain a PCR reaction. PCR amplification is particularly well suited to this use in the apparatus, methods and systems of the invention. Thermocycling amplification methods, including PCR and LCR, are conveniently performed in microscale devices, making iterative fluidic operations involving PCR well suited to use in methods and devices of the present invention (see also, U.S. Pat. Nos. 5,498,392 and 5,587,128 to Willingham et al.). Accordingly, in one preferred embodiment, generation of amplicons such as sequencing templates using PCR, or direct sequencing of nucleic acids by PCR (e.g., using nuclease digestion as described supra) is performed with the integrated systems and devices of the invention.

Thermocycling in microscale devices, including thermocycling by joule heating is described in WO 99/12016, entitled "ELECTRICAL CURRENT FOR CONTROLLING FLUID PARAMETERS IN MICROCHANNELS" published Mar. 11, 1999 by Calvin Chow, Anne R. Kopf-Sill and J. Wallace Parce; in U.S. Pat. No. 5,965,410; in WO 98/45481, entitled "CLOSED-LOOP BIOCHEMICAL ANALYZERS," published Oct. 15, 1998; and in U.S. Pat. No. 6,303,343. In brief, energy is provided to heat fluids, e.g., samples, analytes, buffers and reagents, in desired locations of the substrates in an efficient manner by application of electric current to fluids in microchannels. Thus, the present invention optionally uses power sources that pass electrical current through a first channel region for heating purposes, as well as for material transport. In exemplary embodiments, fluid passes through a channel of a desired cross-section (e.g., diameter) to enhance thermal transfer of energy from the current to the fluid. The channels can be formed on almost any type of substrate material such as, for example, amorphous materials (e.g., glass, plastic, silicon), composites, multi-layered materials, combinations thereof, and the like.

In general, electric current passing through the fluid in a channel produces heat by dissipating energy through the electrical resistance of the fluid. Power dissipates as the current passes through the fluid and goes into the fluid as energy as a function of time to heat the fluid. The following mathematical expression generally describes a relationship between power, electrical current, and fluid resistance:

$$POWER = I^2 R$$

where

POWER=power dissipated in fluid;

I=electric current passing through fluid; and

R=electric resistance of fluid.

The above equation provides a relationship between power dissipated ("POWER") to current ("I") and resistance ("R"). In some of the embodiments, which are directed toward moving fluid in channels, e.g., to provide mixing, electrophoretic separation, or the like, a portion of the power goes into kinetic energy of moving the fluid through the channel. However, it is also possible to use a selected portion of the power to controllably heat fluid in a channel or selected channel regions. A channel region suitable for heating is often narrower or smaller in cross-section than other channel regions in the channel structure, as a smaller cross-section provides higher resistance in the fluid, which increases the temperature of the fluid as electric current passes through. Alternatively, the electric current is increased across the length of the channel by increased voltage, which also increases the amount of power dissipated into the fluid to correspondingly increase fluid temperature.

To selectively control the temperature of fluid at a region of the channel, a power supply applies voltage and/or current in one of many ways. For instance, a power supply can apply direct current (i.e., DC) or alternating current (AC), which passes through the channel and into a channel region which is smaller in cross-section, thereby heating fluid in the region.

This current is selectively adjusted in magnitude to complement any voltage or electric field that is applied to move fluid in and out of the region. AC current, voltage, and/or frequency can be adjusted, for example, to heat the fluid without substantially moving the fluid. Alternatively, a power supply can apply a pulse or impulse of current and/or voltage, which passes through the channel and into a channel region to heat fluid in the region. This pulse is selectively adjusted to complement any voltage or electric field that is applied to move fluid in and out of the region. Pulse width, shape, and/or intensity can be adjusted, for example, to heat the fluid substantially without moving the fluid or to heat the fluid while moving the fluid. Still further, the power supply can apply any combination of DC, AC, and pulse, depending upon the application. In practice, direct application of electric current to fluids in the microchannels of the invention results in extremely rapid and easily controlled changes in temperature.

A controller or computer such as a personal computer monitors the temperature of the fluid in the region of the channel where the fluid is heated. The controller or computer receives current and voltage information from, for example, the power supply and identifies or detects temperature of fluid in the region of the channel. Depending upon the desired temperature of fluid in the region, the controller or computer adjusts voltage and/or current to meet the desired fluid temperature. The controller or computer also can be set to be "current controlled" or "voltage controlled" or "power controlled" depending upon the application.

The region which is heated can be a "coil" which is optionally in a planar arrangement. Transfer of heat from the coil to a reaction channel through a substrate material is used to heat the reaction channel. Alternatively, the coil itself is optionally the reaction channel.

A voltage is applied between regions of the coil to direct current through the fluid for heating purposes. In particular, a power supply provides a voltage differential between regions of the coil. Current flows between the regions and traverses a plurality of coils or coil loops (which can be planar), which are defined by a substrate. Shape and size of the coils can influence an ability of current to heat the fluid in the coil. As current traverses through the fluid, energy is transferred to the fluid for heating purposes. Cooling coils can also be used. As a cooling coil, a fluid traverses from region to region in the coil, which can be placed to permit heat transfer through a substrate from a sample. The cooling fluid can be a variety of substances including liquids and gases. As merely an example, the cooling fluid includes aqueous solutions, liquid or gaseous nitrogen, and others. The cooling fluid can be moved between regions using any of the techniques described herein, and others. Further details are found in Chow et al., supra.

The introduction of electrical current into fluid causes heat (this procedure is referred to as "Joule heating"). In the examples of fluid movement herein where thermal effects are not desired, the heating effect is minimal because, at the small currents employed, heat is rapidly dissipated into the chip itself. By substantially increasing the current across the channel, rapid temperature changes are induced that can be monitored by conductivity. At the same time, the fluid can be kept static in the channel by using alternating instead of direct current. Because nanoliter volumes of fluid have tiny thermal mass, transitions between temperatures can be extremely short. Oscillations between any two temperatures above 0° C. and below 100° C. in 100 milliseconds have been performed.

Joule heating in microchannels is an example of how benchtop methods can be dramatically improved in the formats provided herein. PCR takes hours to perform currently, primarily because it takes a long time for conventional heating blocks to oscillate between temperatures. In addition, reagent cost is an obstacle to massive experimentation. Both these parameters are altered by orders of magnitude in the LabChip™ format.

Figure 2:
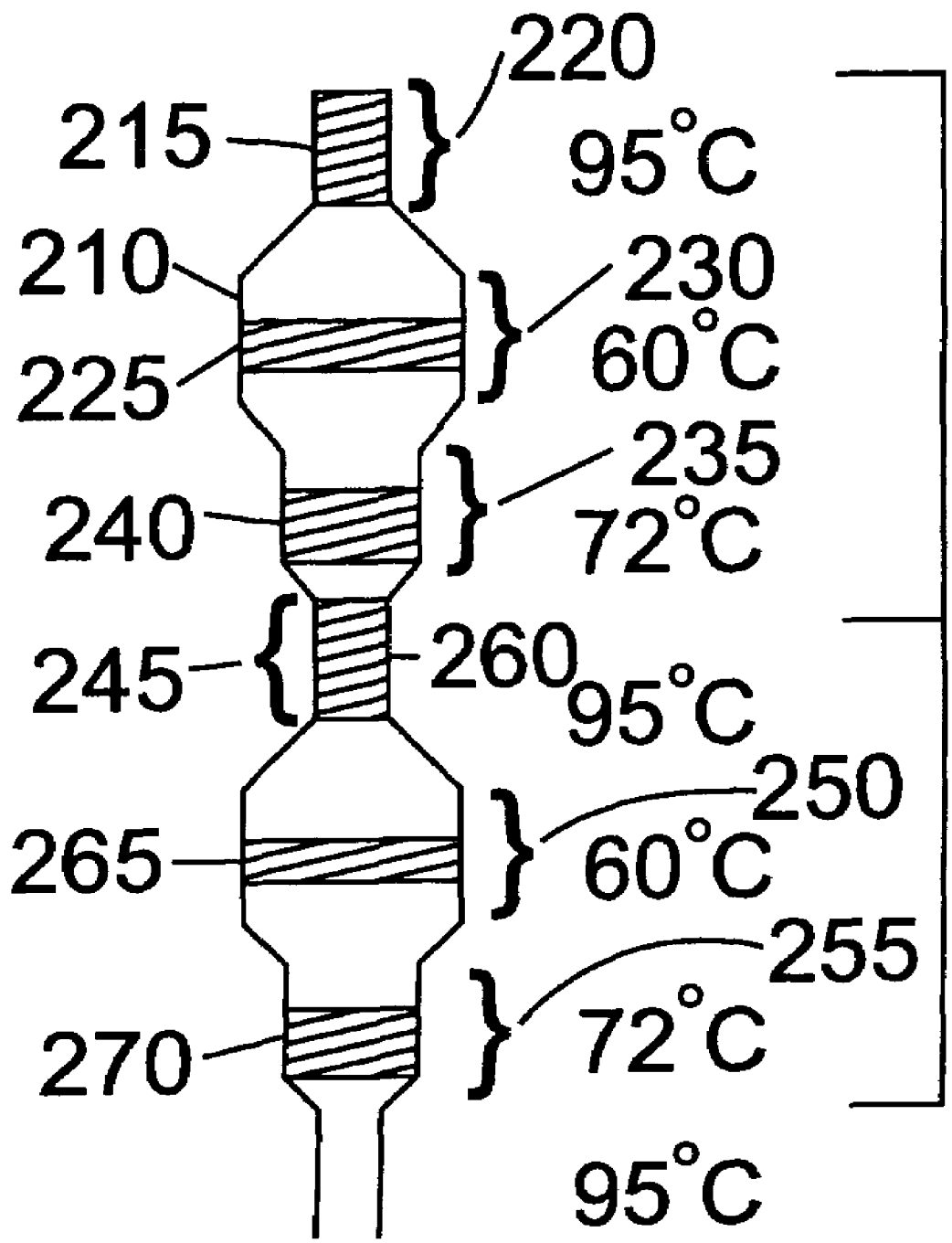
FIG. 2 is a schematic drawing of a microchannel for joule heating.

In one aspect, PCR reaction conditions are controlled as a function of channel geometry. Microfabrication methods permit the manufacture of channels that have precise variations in cross sectional area. Since the channel resistance is inversely proportional to the cross sectional area, the temperature varies with the width and depth of the channel for a given flow of current. As fluid moves through a structure of varying cross sectional area, its temperature will change, depending on the dimensions of the channel at any given point. The amount of time it experiences a given temperature will be determined by the velocity of the fluid flow, and the length of channel with those dimensions. This concept is illustrated in FIG. 2. Nucleic acids of typical lengths have a low diffusion coefficient (about $10^{-7}$ cm/sec$^2$). Thus over the time frame necessary to affect amplification, DNA will only diffuse a few hundred microns. In a given channel, reactions of a few nanoliters will occupy a few millimeters. Thus in devices of convenient length (a few centimeters), many PCR reactions can be performed concurrently yielding new amplification products every few seconds per channel. In parallel formats, hundreds of separate reactions can be performed simultaneously. Because of its simplicity, throughput, and convenience, this amplification unit is a preferred feature of many assays herein.

In FIG. 2, amplification reactions are performed concurrently in series using biased alternating current to heat the fluid inside the channel and move material through it. The time for each step of the reaction is controlled by determining the speed of movement and the length of channel having particular widths. Flow can be reversed to allow a single small channel region to be used for many separate amplifications.

As depicted, several samples are run simultaneously in channel 210. Sample 215 is in narrow channel region 220; in operation, this region is heated to, e.g., 95° C. (hot enough to denature nucleic acids present in sample 215, but cool enough that thermostable reagents such as Taq DNA polymerase are relatively stable due to the relative size of region 220 and the applied current. Concurrently, wide channel region 230 is heated, e.g., to 60° C. (cool enough for binding of primers in sample 225 and initiation of polymerase extension), due to the relative size of region 230 and the applied current. Concurrently, intermediate channel region 235 is heated, e.g., to 72° C. (hot enough to prevent unwanted non-specific primer-target nucleic acid interactions in sample 240 and cool enough to permit continued polymerase extension), due to the relative size of region 235 and the applied current. This process can be concurrently carried out with a plurality of additional channel regions such as narrow region 245, wide region 250 and intermediate region 255, with samples 260, 265 and 270.

Where possible, direct detection of amplified products can be employed. For example, differentially labeled competitive probe hybridization is used for single nucleotide discrimination. Alternatively, molecular beacons or single nucleotide polymerase extension can be employed. Homogeneous detection by fluorescence polarization spectroscopy can also be utilized (fluorescence polarization has been used to distinguish between labeled small molecules free in solution or bound to protein receptors).

The present invention provides the ability to integrate complex functions such as PCR and nucleic acid separation in a single format, e.g., in a microfluidic device. PCR and nucleic acid separations are optionally performed in the same sieving medium, therefore making it possible to perform both functions in a single channel of a microfluidic device.

For example, a Caliper LabChip™ is optionally used to load DNA template, run the PCR reaction, and then size the resulting PCR product by gel separation. FIG. 1 provides a schematic of an example device. Device 100 is optionally filled with a sieving medium as described above, e.g., a sieving gel. The sieving medium provides a continuous fluid phase throughout the device, such that PCR is optionally carried out by joule heating in one channel, e.g., channel 101, and product separation in another channel, e.g., channel 103. Alternatively, the entire device is thermocycled to perform PCR. PCR is thereby carried out in the sieving medium. PCR reagents and a target nucleic acid are added to the sieving medium if not already incorporated therein, e.g., into channel 101. Cross channel 101 is optionally a PCR channel as described herein and shown in FIG. 2. The loaded device is typically placed on a thermocycler (MJ Research) and the temperature is typically cycled to amplify the target nucleic acid. At the end of the cycling procedure, the chip is typically placed on a microscope detection station and the product is electrokinetically injected into separation channel 103. For example, voltages are applied at wells 107 and 109 to electrokinetically separate the product nucleic acids. An example spectrum showing separated nucleic acid peaks is provided in FIG. 3.

It will be appreciated that separations chips comprising a single sieving matrix are produced as described above. However, additional fluidic phases are optionally placed in additional channels or channel regions in fluid communication with a channel region comprising the PCR sieving mixture for electrophoretic or electroosmotic movement of the PCR components or products in the chips. For example, in some aspects a PCR reaction product is selected for further manipulations such as cloning, sequencing or the like, all of which are optionally performed in the same device (see also, U.S. Ser. No. 60/068,311, entitled "Closed Loop Biochemical Analyzer" by Knapp, filed Dec. 19, 1997 and U.S. Pat. No. 6,235,471).

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A method of performing PCR and separating one or more PCR products, the method comprising:
    (i) mixing one or more PCR reaction components with an unpolymerized sieving medium in a channel of a microfluidic device to provide an unpolymerized PCR sieving medium within the channel;
    (ii) thermocycling the PCR sieving medium to produce one or more PCR products;
    (iii) polymerizing the sieving medium after thermocycling is completed, wherein the polymerized sieving medium has a polymer concentration that is less than 0.4%; and
    (iv) separating the one or more PCR products by flowing the one or more PCR products through the polymerized sieving medium.

2. The method of claim 1, wherein the polymer concentration of the polymerized sieving medium is about 0.35% or less.

3. The method of claim 1, wherein the polymer comprises acrylamide.

4. The method of claim 3, wherein the polymer comprises linear acrylamide, polyacrylamide, polydimethylacrylamide, or polydimethylacrylamide/coacrylic acid.

5. The method of claim 1, wherein the polymer comprises polyethylene oxide.

6. The method of claim 1, wherein the one or more PCR reaction components comprise one or more of: a thermostable DNA polymerase, a plurality of nucleotides, a nucleic acid template, a primer which hybridizes to the nucleic acid template, or $Mg^{++}$.

7. The method of claim 1, comprising mixing the PCR reaction components with the sieving medium in a microfluidic channel.

8. The method of claim 7, further comprising separating the one or more PCR products by flowing the one or more PCR products through the sieving medium in the microfluidic channel.

9. The method of claim 1, wherein separating comprises electrophoretically separating.

* * * * *